United States Patent [19]

Grollier

[11] Patent Number: 5,064,442
[45] Date of Patent: Nov. 12, 1991

[54] PROCESS FOR DYEING KERATINOUS FIBRES AND DYEING COMPOSITION USING AN INDOLE DERIVATIVE, A QUINONE DYE AND AN OXIDIZING SYSTEM

[75] Inventor: Jean F. Grollier, Paris, France

[73] Assignee: L'Oreal, Paris, France

[21] Appl. No.: 637,151

[22] Filed: Jan. 3, 1991

Related U.S. Application Data

[63] Continuation of Ser. No. 301,398, Jan. 25, 1989, abandoned.

[30] Foreign Application Priority Data

Jan. 26, 1988 [LU] Luxembourg ............... 87113

[51] Int. Cl.$^5$ ............................. A61K 7/13
[52] U.S. Cl. ............................. 8/407; 8/405; 8/406; 8/409; 8/423; 8/634
[58] Field of Search ............ 8/405, 406, 407, 409, 8/423, 634

[56] References Cited

U.S. PATENT DOCUMENTS

| | | | |
|---|---|---|---|
| 4,776,857 | 10/1988 | Carrol et al. | 8/405 |
| 4,804,385 | 2/1989 | Grollier et al. | 8/406 |
| 4,808,190 | 2/1989 | Grollier et al. | 8/406 |
| 4,822,375 | 4/1989 | Lang et al. | 8/408 |

FOREIGN PATENT DOCUMENTS

| | | |
|---|---|---|
| 3031709 | 4/1982 | Fed. Rep. of Germany ......... 8/406 |
| 2093867 | 9/1982 | United Kingdom . |
| 2110722 | 6/1983 | United Kingdom . |
| 2132643 | 7/1984 | United Kingdom . |
| 2185498 | 7/1987 | United Kingdom . |

Primary Examiner—Paul Lieberman
Assistant Examiner—J. Darland
Attorney, Agent, or Firm—Cushman, Darby & Cushman

[57] ABSTRACT

The invention relates to a process for dyeing keratinous fibres, consisting in applying a composition (A) containing:
- (a) at least one indole derivative,
- (b) a quinone dye chosen from:
    - (i) 1,4-hydroxynaphthoquinones,
    - (ii) benzoquinone derivatives, and
    - (iii) hydroxyanthraquinones.

The color being developed by an oxidizing system consisting of:
- (i) iodide ions and hydrogen peroxide,
- (ii) nitrites,
- (iii) oxidizing agents chosen from periodic acid and periodates, sodium hypochlorite, potassium ferricyanide, silver oxide, Fenton's reagent, lead (IV) oxide, caesium (V) sulphate, ammonium persulphate and ferric chloride, and
- (iv) a permanganate or a dichromate.

39 Claims, No Drawings

PROCESS FOR DYEING KERATINOUS FIBRES AND DYEING COMPOSITION USING AN INDOLE DERIVATIVE, A QUINONE DYE AND AN OXIDIZING SYSTEM

This is a continuation of application Ser. No. 07/301,398, filed Jan. 25, 1989, now abandoned.

The invention relates to a new process for dyeing keratinous fibers, more particularly human keratinous fibers such as hair, with an indole derivative in combination with certain quinone dyes and to the composition used in this process.

It is well known that the natural biosynthesis of eumelanins from tyrosine takes place in a number of steps. One of these consists in the formation of 5,6-dihydroxyindole, which is oxidized to form a pigment which is one of the main constituents of eumelanin.

Many hair-dyeing processes using 5,6-dihydroxyindole or indole derivatives have already been proposed in the past and there is, in particular, a known process which consists in dyeing hair into separate steps, by applying a composition containing, in a suitable medium for dyeing, 5,6-dihydroxyindole in combination either with iodide ions or with hydrogen peroxide, this application being preceded or followed by the application of hydrogen peroxide when 5,6-dihydroxyindole is in combination with iodide ions, or by the application of iodide ions when 5,6-dihydroxyindole is in combination with hydrogen peroxide. A process of this kind is described particularly in Luxembourg Patent Application No. 86,256.

The process is used preferentially by applying, in the first step, a composition containing 5,6-dihydroxyindole in combination with iodide ions, this application being preceded or followed by the application of hydrogen peroxide.

This latter process is particularly noteworthy in its speed and in the fact that it does not degrade the mechanical properties of the hair and in most cases results in black colors or in various shades of grey and, in certain cases, in brown and blond colors. However, it does not make it possible to obtain a sufficiently wide range of various shades, with highlights, and especially various brown and blond shades which can be rich in highlights and are particularly sought after in hair dyeing.

There are also known quinone derivatives such as hydroxynaphthoquinones such as, for example lawsone, which is the dyeing principle of henna, and juqlone, which is the dyeing principle of the walnut tree, as well as benzoquinone derivatives and hydroxyanthraquinones, known for their use in the dyeing of keratinous fibers.

In the past, there has been envisaged employing, for dyeing these fibers, particularly 2-hydroxynaphthoquinone derivatives in French Patent No. 2,517,199, 5-hydroxynaphthoquinone derivatives in French Patent No. 2,537,433, benzoquinone derivatives in French Patent No. 2,517,200, and hydroxyanthraquinones in French Patent No. 2,500,749.

It has now been found, and this is what forms the subject matter of the present invention, that it is possible to obtain various highlight-rich shades by combining, in the same single composition, an indole derivative and at least one quinone derivative chosen from certain hydroxynaphthoquinones, benzoquinones or hydroxyanthraquinones, the color being developed using an oxidizing system, preferably inorganic.

A subject of the invention consists therefore of a process for dyeing keratinous fibers, using an indole derivative and at least one quinone derivative chosen from certain hydroxynaphthoquinones, benzoquinones or hydroxyanthraquinones or mixtures thereof, the color being developed by an oxidizing system.

Another subject of the invention consists of compositions intended to be employed for dyeing keratinous fibers, containing an indole derivative, an iodide or a nitrite and at least one quinone dye from the group of hydroxynaphthoquinones, benzoquinones or hydroxyanthraquinones or else mixtures thereof.

A further subject of the invention is dyeing outfits or kits, containing a number of components allowing the process indicated above to be used.

Other subjects of the invention will become apparent on reading the description and the examples which follow.

The process for dyeing keratinous, preferably human, fibers, in accordance with the invention, is essentially characterized by the application to these of at least one composition (A) containing, in a suitable medium for dyeing, (a) at least one indole derivative corresponding to the formula:

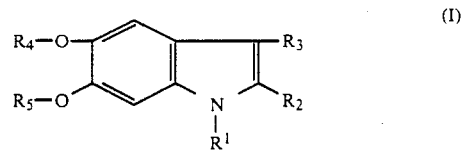

in which:

$R_1$ denotes a hydrogen atom, a lower alkyl group or a $-SiR_6R_7R_8$ group;

$R_2$ and $R_3$, which are identical or different, denote a hydrogen atom or else a lower alkyl group, a carboxyl group, a lower alkoxycarbonyl group or a $-COOSiR_6R_7R_8$ group;

$R_4$ and $R_5$, which are identical or different, denote a hydrogen atom, a linear or branched $C_1-C_{20}$ alkyl group, a formyl group, a linear or branched $C_2-C_{20}$ acyl group, a linear or branched $C_3-C_{20}$ alkenoyl group, a $-SiR_6R_7R_8$ group, a $-P(O)(OR_9)_2$ group, a $R_9OSO_2$ group, or else $R_4$ and $R_5$, together with the oxygen atoms to which they are linked, form a ring which may contain a carbonyl group, a methylene group, a thiocarbonyl group or a group:

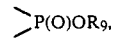

or else

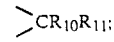

$R_9$ and $R_{10}$ denoting a hydrogen atom or a lower alkyl group, $R_{11}$ denoting a lower alkoxy group or a monoor dialkylamino group, $R_6$, $R_7$ and $R_8$, which are identical or different, denoting linear or branched lower alkyl groups, and addition salts with inorganic or organic acids, as well as the corresponding alkali metal, alkaline-earth metal or amine salts, (b) at least one quinone dye, chosen from the compounds corresponding to the following definitions (i), (ii) and (iii):
(i) 1,4-hydroxynaphthoquinones corresponding to the formula:

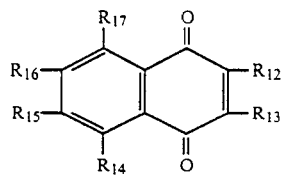

in which:
when $R_{12}$ denotes OH, $R_{13}$ denotes a hydrogen atom, a halogen atom or a hydroxyl, alkoxy, nitro, alkyl or acyl group; $R_{14}$, $R_{15}$, $R_{16}$ and $R_{17}$ denoting, independently of each other, hydrogen or a hydroxyl, alkoxy, alkyl or acyl group;
when $R_{14}$ denotes hydroxyl, $R_{12}$ and $R_{13}$, which are identical or different, denote, independently of each other, a hydrogen atom, a halogen atom, a methyl, methoxy or nitro group, and $R_{15}$ and $R_{16}$, which are identical or different, denote, independently of each other, a hydrogen atom, a hydroxyl group or a methyl or methoxy group, and $R_{17}$ denotes a hydrogen atom or a methyl or methoxy group;
(ii) benzoquinone derivatives of formula:

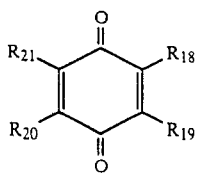

in which:
$R_{18}$, $R_{19}$, $R_{20}$ and $R_{21}$ denote, independently of each other, hydrogen or a hydroxyl, alkoxy, optionally hydroxylated alkyl or an optionally OH-substituted phenyl group, at least one of the groups $R_{18}$, $R_{19}$, $R_{20}$ and $R_{21}$ being other than hydrogen, $R_{18}$ and $R_{21}$, or else $R_{19}$ and $R_{20}$ being incapable of denoting alkyl simultaneously, and when one of the radicals $R_{18}$, $R_{19}$, $R_{20}$ and $R_{21}$ denotes a methyl, hydroxy or methoxy group, at least one of the other substituents is other than hydrogen, and when two of the substituents $R_{18}$, $R_{19}$, $R_{20}$ or $R_{21}$, which are identical, are situated para relative to each other and denote hydroxyl or methoxy, at least one of the other two substituents is other than hydrogen;
(iii) hydroxyanthraquinones chosen from:
1,2-dihydroxyanthraquinone,
1,4-dihydroxyanthraquinone,
1,2,4-trihydroxyanthraquinone,
1,2,7-trihydroxyanthraquinone,
1,2,5,8-tetrahydroxyanthraquinone,
3-carboxy-1,2,4-trihydroxyanthraquinone,
2-carboxy-1-methyl-3,5,6,8-tetrahydroxyanthraquinone,
3-sulpho-1,2,4-trihydroxyanthraquinone,
3-sulpho-1,2-dihydroxyanthraquinone,
5,8-dichloro-1,4-dihydroxyanthraquinone, and
3-hydroxymethylanthraquinone,
the color being developed using an oxidizing system consisting of:
(i) iodide ions and hydrogen peroxide, the composition (A) in this case additionally containing either (a) iodide ions or (b) hydrogen peroxide, and the application of the composition (A) being preceded or followed by the application of a composition (B) which contains, in a suitable medium for dyeing, either:
a) hydrogen peroxide at a pH of between 2 and 12 and preferably between 2 and 7 when the composition (A) contains iodide ions, or:
b) iodide ions at a pH of between 3 and 11 when the composition (A) contains hydrogen peroxide;
(ii) nitrites, the application of the composition (A) being followed by the application of a composition (B) consisting of an aqueous composition exhibiting an acidic pH, the composition (A) or (B) containing at least one nitrite;
(iii) oxidizing agents chosen from periodic acid and periodates, sodium hypochlorite, potassium ferricyanide, silver oxide, Fenton's reagent, lead(IV) oxide, caesium(V) sulphate, ammonium persulphate and ferric chloride, these oxidizing agents being present in the composition (A) or being applied simultaneously or sequentially, separately, preferably after the composition (A) by means of a composition (B) containing them in a suitable medium for dyeing; or else
(iv) permanganates or dichromates, these oxidizing agents being applied by means of an aqueous composition (B), at a pH of 2 to 10, before the application of the composition (A).

The application of the compositions (A) and (B) is preferably separated by a rinsing step.

In the formula (I), the lower alkyl or alkoxy radicals preferably denote $C_1$–$C_6$ radicals.

Among the preferred compounds of the invention there will be mentioned 5,6-dihydroxyindole, 2-methyl-5,6-dihydroxyindole, 5-methoxy-6-hydroxyindole, 5(or 6)-acetoxy-(6 or 5)-hydroxyindole, 2-carboxy-5,6-dihydroxyindole, 3-methyl-5,6-dihydroxyindole, 2,3-dimethyl-5,6-dihydroxyindole and their salts.

In the formula of the quinone dyes (II) and (III) referred to above, the alkyl and alkoxy groups preferably denote groups containing 1 to 6 carbon atoms, and the acyl group preferably denotes a group containing 2 to 4 carbon atoms.

The quinones dyes which are particularly preferred in accordance with the invention are chosen from:
2-hydroxy-1,4-naphthoquinone,
2,5-dihydroxy-1,4-naphthoquinone,
2-hydroxy-3-methoxy-1,4-naphthoquinone,
2,3-dihydroxy-1,4-naphthoquinone,
2,5,7-trihydroxy-1,4-naphthoquinone,
5-hydroxy-1,4-naphthoquinone,
2,5,8-trihydroxy-1,4-naphthoquinone,
2-hydroxy-3-methyl-1,4-naphthoquinone,
2,5-dihydroxy-3-methyl-1,4-benzoquinone,
2,5-dihydroxy-3-methoxy-6-methyl-1,4-benzoquinone,
2-carboxy-1-methyl-3,5,6,8-tetrahydroxyanthraquinone,
1,2-dihydroxyanthraquinone, 1,2,4-trihydroxyanthraquinone, and
3-carboxy-1,2,4-trihydroxyanthraquinone.

In the first alternative form, the iodide ion employed in accordance with the invention is preferably an alkali metal, alkaline-earth metal or ammonium iodide and more particularly potassium iodide.

The proportion of iodide ions in these compositions is preferably between 0.007 and 4% by weight, expressed as $I^-$ ions, and more particularly between 0.08 and 1.5% by weight, expressed as $I^-$ ions relative to the total weight of the composition (A).

The hydrogen peroxide content is generally between 1 and 40 volumes and preferably between 2 and 20 volumes, and more particularly between 3 and 10 volumes.

The weight proportion of the indole derivative in combination with the quinone dye(s) defined above, relative to the iodide ions, is preferably between 0.05 and 10 and more particularly between 0.5 and 2.

In the second alternative form of the process in accordance with the invention, the nitrites which can be used more particularly are:

alkali metal, alkaline-earth metal or ammonium nitrites or nitrites of any other cosmetically acceptable cation when it is employed for dyeing living human hair;

organic nitrite derivatives such as, for example, amyl nitrite;

or else nitrite carriers, that is to say compounds which generate a nitrite when converted.

The nitrites which are particularly preferred are sodium, potassium or ammonium nitrites.

The nitrite anion expressed in the form of $NO_2^-$ is present in sufficient quantities to develop a color with the indole derivative applied in the first step. Its concentration is preferably between 0.02 and 1 mole/liter.

The pH of the composition (A) is preferably between 2 and 10.

The pH of the composition (B) is acidic and allows the color to be controlled. This pH is preferably between 2 and 6 and in particular is adjusted to approximately 3 in the case of short contact times and in the case of the darkest shades.

A preferred embodiment of the invention consists in applying the composition (A) containing the indole derivative in a first step and the composition (B) containing a nitrite in an aqueous acidic medium in a second step.

Another embodiment of the invention may consist in applying, in a first step, a composition (A') containing, in a suitable medium for dyeing, the indole derivative in a neutral or alkaline medium and a nitrite. In this case, the hair is dyed by applying, in a second step, a composition comprising an aqueous medium which is suitable for dyeing, adjusted to a pH which is acidic and preferably between 2 and 6.

According to the third alternative form, the particularly preferred oxidizing agent is sodium periodate. This oxidizing agent is preferably employed in proportions of 3 to 15% by weight relative to the total weight of the composition.

According to the fourth alternative form, potassium permanganate or sodium dichromate is preferably employed, this permanganate or dichromate being preferably employed at a molality higher than $10^{-3}$ mole/1000 g and preferably between $10^{-2}$ mole/1000 g and $10^{-1}$ mole/1000 g.

The pH of the composition containing the permanganate or dichromate anions is preferably between 2 and 5 and is adjusted to these values with inorganic acids.

The process for dyeing keratinous, preferably human, fibers in accordance with the invention is preferably implemented by applying to these fibers at least one composition (A) containing, in a suitable medium for dyeing, at least 5,6-dihydroxyindole, at least one quinone dye defined above, in combination with iodide ions, the application of this composition (A) being preceded or followed by the application of a composition (B) which contains, in a suitable aqueous medium for dyeing, hydrogen peroxide at a pH of between 2 and 12.

The process in accordance with the invention is preferably implemented by applying, in the first step, the composition (A) containing the iodide ions in the form of an alkali metal, alkaline-earth metal or ammonium iodide, the 5,6-dihydroxyindole and the quinone dye(s) defined above, and then, in a second step, after an optional intermediate rinsing, the composition (B) containing hydrogen peroxide.

The process in accordance with the invention is preferably applied to hair dyeing, and particularly to that of living human hair, in which case the medium employed must be cosmetically acceptable.

According to a preferred embodiment, the keratinous fibers are rinsed between the two steps, which, inter alia, enables staining of the scalp to be avoided when the composition is employed for dyeing human hair.

The invention can also be used without intermediate rinsing, and this allows the application times to be notably shortened.

The composition (A) employing the process according to the invention, and which constitutes another subject of the invention, is essentially characterized in that it contains, in a suitable medium for dyeing, the indole derivative of formula (I), at least one quinone dye such as defined above and at least iodide or nitrite ions.

In the compositions employed in accordance with the invention, the indole derivative of formula (I) is generally present in proportions of between 0.01 and 5% by weight and preferably between 0.03 and 3% by weight relative to the total weight of the composition (A).

The proportion of quinone dye of formula (II), defined above, is preferably between 0.01 and 5% by weight, and in particular between 0.05 and 3% by weight relative to the total weight of the composition (A).

The dyeing process in accordance with the invention is used by providing application times, for the various compositions applied in each of the process steps, of between 10 seconds and 45 minutes and preferably of the order of 2 to 25 minutes and more particularly of the order of 2 to 10 minutes.

The applicant has been able to ascertain that the dyeing carried out by virtue of the process in accordance with the invention made it possible to obtain guide colorings, penetrating well into the fibers, especially human keratinous fibers such as hair, without damaging them. Furthermore, these colors exhibit an improved resistance to external agents or to permanent waving treatment, in particular a superior resistance to light and/or to washing, relative to the colors obtained either with 5,6-dihydroxyindole by itself or with the quinone dye by itself, when these are employed with the iodide ion, using a hydrogen peroxide composition.

It has also been possible to note that hair dyed a number of times following fresh growth by virtue of the processes and of the compositions used, according to the invention, was softer, more shiny, and had better mechanical properties than hair dyed using processes and the compositions of the prior art.

The compositions used in the process according to the invention may be in various forms such as more or less thickened or gelled liquid, cream, emulsion or foam and may, if desired, be packaged in aerosol devices, or else in other suitable forms for producing the dyeing.

The medium which is suitable for dyeing is preferably an aqueous medium consisting of water or of a water-solvent(s) mixture. The solvents are chosen from organic solvents and preferably from ethyl alcohol, propyl or isopropyl alcohol, tert-butyl alcohol, ethylene glycol, ethylene glycol monomethyl, monoethyl and monobutyl ethers, ethylene glycol monoethyl ether acetate, propylene glycol, propylene glycol and dipropylene glycol monomethyl ethers, and methyl lactate. The solvents which are particularly preferred are ethyl alcohol, propylene glycol and ethylene glycol monoethyl and monobutyl ethers.

According to another embodiment, the suitable medium for dyeing may consist of anhydrous solvents such as those defined above, the composition in this case being either mixed with an aqueous medium at the time of use, or applied to keratinous fibers wetted with an aqueous composition beforehand. In accordance with the invention, a medium or a solvent containing less than 1% of water is called an anhydrous medium or solvent.

When the suitable medium for dyeing consists of a water-solvent(s) mixture, the solvents are preferably employed in concentrations of between 0.5 and 75% by weight relative to the total weight of the composition, in particular between 2 and 50% and more particularly between 2 and 20% by weight.

The compositions employed in accordance with the invention may contain any other adjuvants which are usually employed in dyeing keratinous fibers, and in particular cosmetically acceptable adjuvants when these compositions are applied for dyeing living human hair.

In this latter case, the compositions may particularly contain fatty amides in preferred proportions of 0.05 to 10% by weight, anionic, cationic, nonionic or amphoteric surface-active agents or mixtures thereof, which are preferably present in proportions of between 0.1 and 50% by weight, thickeners present preferably in proportions of between 0.1 and 5% by weight, perfumes, sequestering agents, film-forming agents, treatment agents, dispersing agents, conditioning agents, preserving agents, opacifying agents and agents for swelling keratinous fibers.

The thickeners may be chosen more particularly from sodium alginate, gum arabic, guar gum, biopolymers such as xanthan gum or scleroglucans, cellulose derivatives such as methyl cellulose, hydroxyethyl cellulose, hydroxypropyl methyl cellulose, and sodium salts of carboxymethyl cellulose and of optionally crosslinked acrylic acid polymers. Inorganic thickening agents such as bentonite may also be employed.

The alkalizing agents which can be employed in these compositions may be, in particular, amines such as alkanolamines, alkylamines, and alkali metal or ammonium hydroxides or carbonates.

The acidifying agents which can be employed in these compositions may be chosen rom lactic acid, acetic acid, tartaric acid, phosphoric acid, hydrochloric acid and citric acid.

It is obviously possible to employ any other alkalizing or acidifying agent which is acceptable, particularly in cosmetics in the case of hair dyeing.

When the composition is employed in the form of foam, it can be packaged under pressure in an aerosol device in the presence of a propellent agent and of at least one foam generator. The foam generators may be anionic, cationic, nonionic or amphoteric foaming polymers or mixtures thereof or surface-active agents of the type defined above.

A particularly preferred embodiment of the invention consists in separately storing, on the one hand, a composition (A1) containing the indole derivative of formula (I) with the iodides in a water/solvent medium or in an anhydrous organic solvent such as defined above and, on the other hand, a composition (A2) containing the quinone dye(s) in solvents or a mixture of anhydrous solvents which may be different, particularly of the type of those defined in French Patent No. 2,526,031, and more particularly saturated monoalcohols such as ethanol and isopropanol and saturated long-chain monoalcohols such as cetyl alcohol; polyols such as, for example, alkylene glycols such as ethylene glycol, propylene glycol, glycerol and diethylene glycol; glycol ethers such as mono-, di- and triethylene glycol monoalkyl ethers such as, for example, ethylene glycol monoethyl ether, ethylene glycol monobutyl ether and diethylene glycol monoethyl ether; esters such as ethylene glycol monomethyl ether acetate and ethylene glycol monoethyl ether acetate; and esters of saturated fatty acids and of saturated lower alcohols, such as isopropyl myristate or palmitate. The solvents which are more particularly preferred are ethanol, cetyl alcohol, propylene glycol and ethylene glycol monoethyl and monobutyl ethers.

When it is envisaged to employ the composition containing hydrogen peroxide as composition (A), then the following can be stored separately, as indicated above:
 (a) a composition (A'1) containing 5,6-dihydroxyindole in a suitable medium for dyeing;
 (b) a composition (A'2) containing the quinone dye(s) in a suitable medium for dyeing; and
 (c) a composition (A'3) containing hydrogen peroxide in solution in a suitable medium for dyeing.

These dye or oxidizing agent solutions which are stored separately can be mixed just before use.

With a view to using the process in accordance with the invention, the various compositions may be packaged in a multicompartment device, also called a dyeing kit or outfit, comprising all the components intended to be applied, in the case of the same single dyeing operation, to the keratinous fibers, in successive applications with or without premixing.

Such devices are known per se and may comprise a first compartment containing the composition (A) containing the indole derivative of formula (I), the quinone dye(s) defined above, in the presence of iodide ions, in a suitable medium for dyeing and, in a second compartment, the composition (B) based on hydrogen peroxide.

A device which is particularly well adapted for using the invention consists of a dispensing assembly of the type of those described in French Patent Application No. 2,586,913, comprising two separate pouches assembled in a pliable case, the two pouches containing, in the case of one, at least the quinone dye in an anhydrous solvent such as defined above, and in the case of the other, at least the indole derivative of formula (I) and the iodide in a water-solvent(s) medium, also defined above.

The multicompartment devices employed according to the invention may be equipped with a third, a fourth and optionally a fifth compartment, especially when the media employed for the composition (A) based on the indole derivative of formula (I) and/or the quinone dye(s) are anhydrous media. In this case, before use a mixture is made up with an aqueous substrate which is suitable for dyeing, present in another compartment.

According to another embodiment of the invention, the composition (A) containing the indole derivative of formula (I), the quinone dye(s) and the iodide ion, in an anhydrous solvent medium, may be applied directly to moist keratinous fibers.

The multicompartment devices or kits employed in accordance with the invention may be equipped with means for mixing at the time of use, which are known per se, and their contents may be packaged under an inert atmosphere.

The process and the compositions employed in accordance with the invention may be used for dyeing natural or already dyed hair, permanent-waved or not or straightened, or hair which has been heavily or lightly bleached and possibly permanent-waved. It is also possible to employ them for dyeing furs or wool.

The examples which follow are intended to illustrate the invention without, however, being limiting in nature.

EXAMPLE 1

Natural grey hair containing 90% of white is dyed by applying two compositions (A) and (B) successively and rinsing between the two applications.

The following compositions (A1), (A2) and (B) are packaged in a three-compartment device or kit:

| Composition (A1) | |
|---|---|
| 5,6-Dihydroxyindole | 0.15 g |
| Potassium iodide | 0.15 g |
| Ethyl alcohol | 2.00 g |
| Citric acid q.s. pH = 5 | |
| Water q.s. | 100.00 g |

| Composition (A2) | |
|---|---|
| 2,5-Dihydroxy-1,4-naphthoquinone | 0.80 g |
| Absolute ethyl alcohol | 30.00 g |
| Citric acid | 1.00 g |
| Nonylphenol oxyethylenated with 9 moles of ethylene oxide q.s. | 100.00 g |

Composition (B)

20-volume aqueous solution of hydrogen peroxide, pH = 3.

A composition (A) is produced by mixing 80 g of the composition (A1) with 20 g of the composition (A2) at the time of use.

The mixture obtained is applied to the hair.

After 15 minutes' application, the hair is rinsed with water and this is followed by the application of the composition (B) for 5 minutes.

After rinsing and drying, the hair has a coppery light blond color.

EXAMPLE 2

Natural grey hair containing 90% of white is colored by applying two compositions (A) and (B) successively and by rinsing between the two applications.

The following compositions (A1), (A2) and (B) are packaged in a 3-compartment device or kit:

| Composition (A1) | |
|---|---|
| 5,6-Dihydroxyindole | 0.25 g |
| Potassium iodide | 0.15 g |
| Guar gum sold under the name Jaguar HP 60 by Celanese | 1.00 g |
| Glycoside alkyl ether sold at a concentration of 60% AS under the name Triton CG 110 by Seppic | 5.00 g AS |
| Ethylene glycol monobutyl ether | 3.00 g |
| Natural pH = 6.5 | |
| Preservative q.s. | |
| Water q.s. | 100.00 g |

| Composition (A2) | |
|---|---|
| 2-Hydroxy-1,4-naphthoquinone | 1.50 g |
| Absolute ethyl alcohol | 30.00 g |
| Citric acid | 1.00 g |
| Nonylphenol oxyethylenated with 9 moles of ethylene oxide q.s. | 100.00 g |

| Composition (B) | |
|---|---|
| Hydrogen peroxide | 3.75 g |
| Ammonium lauryl sulphate | 6.70 g |
| Gum arabic | 1.00 g |
| Perfume q.s. | |
| 2-Amino-2-methyl-1-propanol q.s. pH = 4 | |
| Water q.s. | 100.00 g |

A composition (A) is produced by ad hoc mixing of 80 g of the composition (A1) with 20 g of the composition (A2).

The mixture is applied to the hair.

After 20 minutes' application, the hair is rinsed and the composition (B) is then applied for 5 minutes.

After rinsing and drying, a coppery golden blond color is obtained.

EXAMPLE 3

Natural grey hair containing 90% of white is colored by applying two compositions (A) and (B) successively and by rinsing between the two applications.

The following compositions (A1), (A2) and (B) are packaged in a three-compartment device or kit:

| Composition (A1) | |
|---|---|
| 5,6-Dihydroxyindole | 0.20 g |
| Potassium iodide | 0.20 g |
| Propylene glycol | 2.00 g |
| Citric acid q.s. pH = 5.5 | |
| Water q.s. | 100.00 g |

| Composition (A2) | |
|---|---|
| 2,5-Dihydroxy-3-methyl-1,4-benzoquinone | 1.00 g |
| Absolute ethyl alcohol | 25.00 g |
| Propylene glycol | 5.00 g |
| Citric acid | 1.20 g |

-continued

| Composition (A2) | |
|---|---|
| Nonylphenol oxyethylenated with 9 moles of ethylene oxide q.s. | 100.00 g |

Composition (B)

10-volume aqueous solution of hydrogen peroxide, pH=3.

A composition (A) is produced by ad hoc mixing of 80 g of the composition (A1) and of 20 g of the composition (A2).

This composition is applied to the hair.

After an application of 15 minutes, the hair is rinsed with water and the composition (B) is applied for 4 minutes.

After rinsing and drying, the hair is dyed lightbeige blond.

EXAMPLE 4

Natural grey hair containing 90% of white is colored by applying two compositions (A) and (B) successively and by rinsing between the two applications.

| Composition (A) | |
|---|---|
| 5,6-Dihydroxyindole | 0.24 g |
| Sodium iodide | 0.20 g |
| Ethyl alcohol | 6.50 g |
| 2,5-Dihydroxy-3-methyl-1,4-benzoquinone | 0.20 g |
| 2-Hydroxy-1,4-naphthoquinone | 0.20 g |
| Ethylene glycol monobutyl ether | 0.60 g |
| Citric acid | 0.30 g |
| Nonylphenol oxyethylenated with 9 moles of ethylene oxide | 13.70 g |
| Water q.s. | 100.00 g |

Composition (B)

That of Example 2 is employed.

The composition (A) is applied to the hair for 10 minutes.

After rinsing with water the hydrogen peroxide composition (B) is applied for 5 minutes.

After rinsing and drying, a beige light-golden blond shade is obtained.

EXAMPLE 5

The procedure is as in Example 4, but with the hydrogen peroxide composition (B) applied before the dye composition (A).

A coppery light-mahogany blond shade is obtained.

EXAMPLE 6

Natural grey hair containing 90% of white is colored by applying two compositions (A) and (B) successively and by rinsing between the two applications.

| Composition (A) | |
|---|---|
| 5,6-Dihydroxyindole | 0.15 g |
| Potassium iodide | 0.10 g |
| Ethyl alcohol | 10.00 g |
| 2-Carboxy-1-methyl-3,5,6,8-tetrahydroxy-anthraquinone | 0.10 g |
| 2,5-Dihydroxy-3-methoxy-6-methyl-1,4-benzoquinone | 0.30 g |
| Polyethylene glycol containing 6 moles of ethylene oxide | 12.00 g |

-continued

| Composition (A) | |
|---|---|
| Water q.s. | 100.00 g |

Composition (B)

20-volume aqueous solution of hydrogen peroxide, pH=3.

The composition (A) is applied to the hair for 15 minutes.

After rinsing with water, the hydrogen peroxide composition (B) is applied for 5 minutes.

After rinsing and drying, a matt golden blond color is obtained.

EXAMPLE 7

Example 2 is reproduced by packaging the compositions (A1) and (A2) in a device such as described in French Patent No. 2,586,913, that is to say in two separate pouches assembled in a pliable case in the end of which an incision is made to deliver directly onto the hair 80 g of the composition (A1) and 20 g of the composition (A2), the composition (A2) containing in addition, relative to Example 2, 1.8% by weight of a thickener: hydroxypropyl cellulose sold under the name Klucel G by Hercules.

EXAMPLE 8

| Composition (A) | |
|---|---|
| Sodium iodide | 0.20 g |
| Ethyl alcohol | 5.00 g |
| Propylene glycol | 5.00 g |
| Xanthan gum sold under the name of Rhodopol SC by Rhone-Poulenc | 1.50 g |
| Preservative q.s. | |
| Triethanolamine q.s. pH = 6.5 | |
| Demineralized water q.s. | 100.00 g |

| Composition (B) | |
|---|---|
| 5,6-Dihydroxyindole | 0.20 g |
| 2,5-Dihydroxy-1,4-naphthoquinone | 0.20 g |
| 2-Hydroxy-1,4-naphthoquinone | 0.15 g |
| Ethanol | 18.00 g |
| Hydroxypropyl cellulose sold under the name of Klucel G by Hercules | 0.60 g |
| Lactic acid | 0.50 g |
| Nonylphenol containing 9 moles of ethylene oxide q.s. | 100.00 g |

The composition (A) is applied for 15 minutes to natural grey hair containing 90% white. After rinsing, a mixture of equal weights of the composition (B) and of 20-volume hydrogen peroxide at pH 3 is applied for 15 minutes. Rinsing and drying is carried out. Hair colored a beige blond shade is then obtained.

EXAMPLE 9

| Composition (A1) | |
|---|---|
| 5-Acetoxy-6-hydroxyindole | 0.20 g |
| Ethanol | 11.00 g |
| Guar gum sold under the name of Jaguar HP 60 by Celanese | 1.00 g |
| Glycoside alkyl ether sold in a concentration of 60% AS under the name of Triton CG 110 by Seppic | 5.00 g AS |

-continued

| Composition (A1) | |
|---|---|
| Preservatives q.s. | |
| Citric acid q.s. pH = 6 | |
| Demineralized water q.s. | 100.00 g |

| Composition (A2) | |
|---|---|
| 2-Hydroxy-1,4-naphthoquinone | 1.50 g |
| Absolute ethyl alcohol | 30.00 g |
| Citric acid | 1.00 g |
| Nonylphenol containing 9 moles of ethylene oxide q.s. | 100.00 g |

| Composition (B) | |
|---|---|
| Sodium metaperiodate | 3.50 g |
| Ethyl alcohol | 5.00 g |
| Citric acid q.s. pH = 4 | |
| Demineralized water q.s. | 100.00 g |

80 g of the composition (A1) are mixed with 20 g of the composition (A2) at the time of use. The mixture obtained is applied for 20 minutes to natural grey hair containing 90% white. The hair is then rinsed and the composition (B) is then applied for 15 minutes. Another rinsing and drying are carried out. The hair is colored a coppery blond shade.

EXAMPLE 10

| Composition (A) | |
|---|---|
| Potassium permanganate | 0.40 g |
| Hydrochloric acid q.s. pH = 3 | |
| Water q.s. | 100.00 g |

| Composition (B) | |
|---|---|
| 5,6-Dihydroxyindole | 0.35 g |
| 2-Hydroxy-3-methyl-1,4-naphthoquinone | 0.20 g |
| 2,5-Dihydroxy-1,4-naphthoquinone | 0.15 g |
| Ethylene glycol monoethyl ether | 12.00 g |
| Polyethylene glycol containing 6 moles of ethylene oxide | 15.00 g |
| Triethanolamine q.s. pH = 5 | |
| Demineralized water q.s. | 100.00 g |

The composition (A) is applied for 15 minutes to natural grey hair containing 90% white and is then rinsed off. The composition (B) is then applied for 20 minutes and another rinsing is carried out. After drying, the hair is dyed a chestnut brown shade with a tendency to mattness.

EXAMPLE 11

| Composition (A1) | |
|---|---|
| 2-Methyl-5,6-dihydroxyindole hydrobromide | 0.25 g |
| Potassium iodide | 0.25 g |
| Propylene glycol | 10.00 g |
| Hydroxyethyl cellulose sold under the name of Natrosol 250 HHR by Aqualon | 1.50 g |
| Preservative q.s. | |
| Triethanolamine q.s. pH = 6 | |
| Demineralized water q.s. | 100.00 g |

| Composition (A2) | |
|---|---|
| 2-Hydroxy-1,4-naphthoquinone | 1.00 g |
| 2,5-Dihydroxy-1,4-naphthoquinone | 0.50 g |
| Absolute ethyl alcohol | 30.00 g |
| Citric acid | 1.00 g |
| Nonylphenol oxyethylenated with 9 moles of ethylene oxide q.s. | 100.00 g |

The ad hoc mixture of the compositions (A1) and (A2) in a weight ratio of 4/1 is applied to natural grey hair containing 90% of white.

After 15 minutes' application, the hair is rinsed and a 20-volume $H_2O_2$ solution of hydrogen peroxide at pH 3 is then applied for 5 minutes. After rinsing and drying, the hair is colored an iridescent light coppery blond shade.

EXAMPLE 12

| Composition (A) | |
|---|---|
| 5,6-Dihydroxyindole | 0.20 g |
| 2-Hydroxy-3-methoxy-1,4-naphthoquinone | 0.15 g |
| Ethanol | 6.50 g |
| Propylene glycol | 2.00 g |
| Nonylphenol oxyethylenated with 9 moles of ethylene oxide | 14.00 g |
| Citric acid q.s. pH = 4.5 | |
| Demineralized water q.s. | 100.00 g |

| Composition (B) | |
|---|---|
| Sodium nitrite | 2.00 g |
| Hydrochloric acid q.s. pH = 3.8 | |
| Demineralized water q.s. | 100.00 g |

The composition (A) is applied for 20 minutes to natural grey hair containing 90% of white. After rinsing, the composition (B) is then applied for 5 minutes, before rinsing again. After drying, the hair is colored a dark golden blond shade.

EXAMPLE 13

| Composition (A) | |
|---|---|
| 5,6-Dihydroxyindole | 0.30 g |
| 2,3-Dihydroxy-1,4-naphthoquinone | 0.10 g |
| 2,5-Dihydroxy-3-methoxy-6-methyl-1,4-benzoquinone | 0.10 g |
| 1,2,4-Trihydroxyanthraquinone | 0.01 g |
| Ethylene glycol monobutyl ether | 12.00 g |
| Nonylphenol oxyethylenated with 9 moles of ethylene oxide | 20.00 g |
| Citric acid | 0.10 g |
| Demineralized water q.s. | 100.00 g |

| Composition (B) | |
|---|---|
| Sodium metaperiodate | 3.50 g |
| Ethyl alcohol | 5.00 g |
| Citric acid q.s. pH = 4 | |
| Demineralized water q.s. | 100.00 g |

The composition (A) is applied for 20 minutes to natural grey hair containing 90% of white. After rinsing, the composition (B) is applied for 15 minutes. After rinsing and drying are carried out. The hair is colored a matt golden blond shade.

EXAMPLE 14

| Composition (A) | |
|---|---|
| 5,6-Dihydroxyindole | 0.15 g |
| Potassium iodide | 0.15 g |
| 2-Hydroxy-1,4-naphthoquinone | 0.15 g |
| Ethyl alcohol | 15.00 g |
| Hydroxypropyl cellulose sold under the name of Klucel G by Hercules | 1.00 g |
| Lactic acid | 0.20 g |
| Demineralized water q.s. | 100.00 g |

This composition is applied for 20 minutes to natural grey hair containing 90% of white. After rinsing, the hair is treated with 20-volume hydrogen peroxide adjusted to pH 8 with triethanolamine before use. After 10 minutes' application, another rinsing and drying are carried out. The hair is then colored a slightly coppery dark golden blond shade.

I claim:

1. A process for dyeing keratinous fibers comprising applying to said fibers at least one composition (A) containing in a medium suitable for dyeing said fibers, (a) at least one indole derivative having the formula

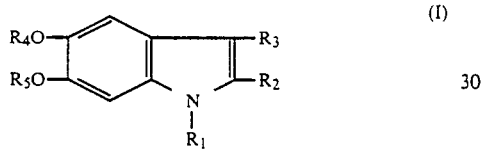

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or $-COOSiR_6R_7R_8$, $R_4$ and $R_5$, each independently, represent hydrogen, linear or branched $C_1$–$C_{20}$ alkyl, formyl, linear or branched $C_2$–$C_{20}$ acyl, linear or branched $C_3$–$C_{20}$ alkenoyl, $-SiR_6R_7R_8$, $-P(O)(OR_9)_2$ or $R_9OSO_2$, or $R_4$ and $R_5$ together with the oxygen atoms to which they are attached form a ring optionally containing a carbonyl group, a methylene group, a thiocarbonyl group, a

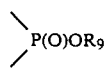

group or a

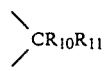

group.

$R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole derivative being present in said composition (A) in an amount ranging from 0.01 to 5 percent by weight based on the total weight of said composition (A), (b) at least one quinone dye selected from the group consisting of (i) 1,4-hydroxynaphthoquinone having the formula

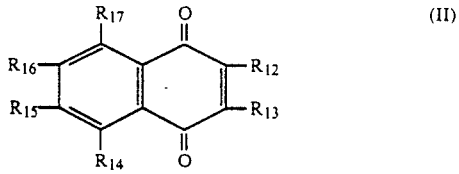

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

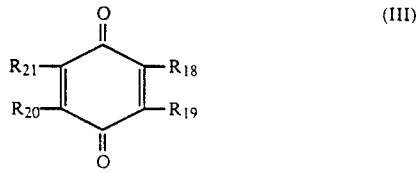

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4-trihydroxyanthraquinone, 1,2,7-trihydroxyanthraquinone, 1,2,5,8-tetrahydroxyanthraquinone, 3-carboxyl-1,2,4-trihydroxyanthraquinone, 2-carboxyl-1-methyl-3,5,6,8-tetrahydroxyanthraquinone, 3-sulpho-1,2,4-trihydroxyanthraquinone, 3-sulpho-1,2-dihydroxyanthraquinone, 5,8-dichloro- 1,4-dihydroxyanthraquinone and 3-hydroxymethylanthraquinone, said quinone dye being present in said composition (A) in an amount ranging from 0.01 to 5 percent by weight based on the total weight of said composition (A), developing a color on said fibers using an oxidizing system selected from the group consisting of:

(i) a source of iodide ions and hydrogen peroxide, in which case said composition (A) contains either (a) a source of iodide ions or (b) hydrogen peroxide and the application of said composition (A) is preceded or followed by the application of composition (B) comprising in a medium suitable for dyeing said fibers (a') hydrogen peroxide at a pH ranging from 2 to 12 when said composition (A) contains a source of iodide ions, or (b') a source of iodide ions at a pH ranging from 3 to 11 when said composition (A) contains hydrogen peroxide;

(ii) a nitrite source, in which case the application of said composition (A) is followed by the application of composition (B') comprising an aqueous composition having an acidic pH, said composition (A) or said composition (B') containing at least one said nitrite source;

(iii) an oxidizing agent selected from the group consisting of periodic acid, a periodate, sodium hypochlorite, potassium ferricyanide, silver oxide, Fenton's reagent, lead (IV) oxide, cesium (V) sulphate, ammonium persulfate and ferric chloride, said oxidizing agent being present in said composition (A) or being applied to said fibers simultaneously or sequentially, separately in a composition (B") comprising a medium suitable for dyeing said fibers and said oxidizing agent; and (iv) an oxidizing agent selected from the group consisting of a permanganate and a dichromate, said oxidizing agent being present in an aqueous composition (B''') having a pH ranging from 2 to 10, said composition (B''') being applied to said fibers prior to the application of said composition (A) thereto.

2. The process of claim 1 wherein said source of iodide ions is selected from the group consisting of an alkali metal iodide, an alkaline earth metal iodide and ammonium iodide.

3. The process of claim 2 wherein the amount of said iodide ions ranges between 0.007 and 4 percent by weight, expressed as $I^-$ ions, relative to the total weight of said composition.

4. The process of claim 2 wherein the amount of said iodide ions ranges between 0.08 and 1.5 percent by weight, expressed as $I^-$ ions, relative to the total weight of said composition.

5. The process of claim 1 wherein the hydrogen peroxide content is between 1 and 40 volumes.

6. The process of claim 1 wherein the hydrogen peroxide content is between 2 and 20 volumes.

7. The process of claim 1 wherein the weight ratio of said indole derivative of formula (I) combined with said quinone dye relative to said iodide ions ranges from 0.05 to 10.

8. The process of claim 1 wherein the weight ratio of said indole derivative of formula (I) combined with said quinone dye relative to said iodide ions ranges from 0.5 to 2.

9. The process of claim 1 wherein said nitrite source is selected from the group consisting of an alkali metal nitrite, an alkaline earth metal nitrite, an ammonium nitrite, and an organic nitrite.

10. The process of claim 1 wherein said nitrite, expressed in the form of $NO_2^-$, is present in an amount ranging from 0.02 to 1 mole/liter.

11. The process of claim 1 wherein said oxidizing system is sodium periodate.

12. The process of claim 1 wherein said permanganate is potassium permanganate present in an amount greater than $10^{-3}$ mole/1000 g.

13. The process of claim 1 wherein said dichromate is sodium dichromate present in an amount greater than $10^{-3}$ mole/1000 g.

14. The process of claim 1 wherein said indole derivative is selected from the group consisting of 5,6-dihydroxyindole, 2-methyl-5,6-dihydroxyindole, 5-methoxy-6-hydroxyindole, 5-acetoxy-6-hydroxyindole, 6-acetoxy-5-hydroxyindole, a mixture of 5-acetoxy-6-hydroxyindole and 6-acetoxy-5-hydroxyindole, 2-carboxy-5,6-dihydroxyindole, 3-methyl-5,6-dihydroxyindole and 2,3-dimethyl-5,6-dihydroxyindole and a salt thereof.

15. The process of claim 1 wherein said quinone dye is selected from the group consisting of 2-hydroxy-1,4-naphthoquinone, 2,5-dihydroxy-1,4-naphthoquinone, 2-hydroxy-3-methoxy-1,4-naphthoquinone, 2,3-dihydroxy-1,4-naphthoquinone, 2,5,7-trihydroxy-1,4-naphthoquinone, 5-hydroxy-1,4-naphthoquinone, 2,5,8-trihydroxy-1,4-naphthoquinone, 2-hydroxy-3-methyl-1,4-naphthoquinone, 2,5-dihydroxy-3-methyl-1,4-benzoquinone, 2,5-dihydroxy-3-methoxy-6-methyl-1,4-benzoquinone, 2-carboxy-1-methyl-3,5,6,8-tetrahydroxyanthraquinone, 1,2-dihydroxyanthraquinone, 1,2,4-trihydroxyanthraquinone and 3-carboxyl-1,2,4-trihydroxyanthraquinone.

16. A process for dyeing keratinous fibers comprising applying to said fibers at least one composition (A) containing in a medium suitable for dyeing said fibers (a) at least 5,6-dihydroxyindole in an amount ranging from 0.01 to 5 percent by weight based on the total weight of composition (A), (b) at least one quinone dye selected from the group consisting of (i) 1,4-hydroxynaphthoquinone having the formula

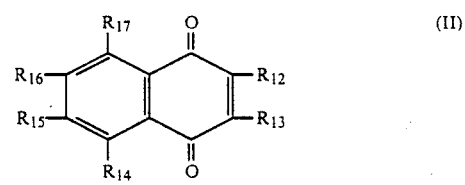

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

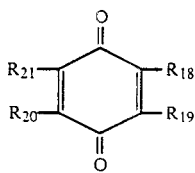

(III)

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4-trihydroxyanthraquinone, 1,2,7-trihydroxyanthraquinone, 1,2,5,8-tetrahydroxyanthraquinone, 3-carboxy-1,2,4-trihydroxyanthraquinone, 2-carboxy-1-methyl-3,5,6,8-tetrahydroxyanthraquinone, 3-sulpho-1,2,4-trihydroxyanthraquinone, 3-sulpho-1,2-dihydroxyanthraquinone, 5,8-dichloro-1,4-dihydroxyanthraquinone and 3-hydroxymethylanthraquinone; wherein said quinone is present in an amount raging from 0.01 to 5 percent by weight based on the total weight of composition (A), and (c) a source of iodide ions or hydrogen peroxide, the application of said composition (A) being preceded or followed by the application to said fibers of composition (B) containing in an aqueous medium suitable for dyeing said fibers either (1) hydrogen peroxide at a pH ranging from 2 to 12 when said composition (A) contains said source of iodide ions, or (2) a source of iodide ions at a pH ranging from 3 to 11 when said composition (A) contains hydrogen peroxide.

17. The process of claim 16 which comprises applying to said fibers, in a first step, said composition (A) containing said 5,6-dihydroxyindole, said quinone dye and said source of iodide ions in the form of an alkali metal iodide, an alkaline earth metal iodide or ammonium iodide and, in a second step, applying said composition (B) containing hydrogen peroxide and having a pH ranging from 2 to 12.

18. The process of claim 1 wherein the steps of said process are separated by a rinsing step.

19. The process of claim 1 wherein the steps of said process are carried out without an intermediate rinsing step.

20. The process of claim 1 wherein the different compositions (A) and (B) are permitted to remain in contact with said fibers for a period of time ranging from 10 seconds to 45 minutes.

21. The process of claim 1 wherein the different compositions (A) and (B) are permitted to remain in contact with said fibers for a period of time ranging from 2 to 25 minutes.

22. The process of claim 1 wherein said indole derivative is present in said composition (A) in an amount ranging from 0.03 to 3 percent by weight based on the total weight of said composition (A).

23. The process of claim 1 wherein said quinone dye is present in said composition (A) in an amount ranging from 0.05 to 3 percent by weight based on the total weight of said composition (A).

24. The process of claim 1 wherein said medium suitable for dyeing said fibers is an aqueous medium comprising water or a mixture of water and an organic solvent.

25. The process of claim 1 wherein said medium suitable for dyeing said fibers is an anhydrous solvent.

26. The process of claim 24 wherein said organic solvent is selected from the group consisting of ethyl alcohol, propyl alcohol, isopropyl alcohol, tert. butyl alcohol, ethylene glycol, ethylene, glycol monomethyl ether, ethylene glycol monoethyl ether, ethylene glocol monobutyl ether, ethylene glycol monoethyl ether acetate, propylene glycol, propylene glycol monomethyl ether, dipropylene glycol monomethyl ether and methyl lactate.

27. The process of claim 25 wherein said anhydrous solvent is selected from the group consisting of ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol, propylene glycol monomethyl ether, dipropylene glycol monomethyl ether and methyl lactate.

28. The process of claim 1 wherein one or more of said compositions also include at least one adjuvant selected from the group consisting of a fatty amide; an anionic, cationic, nonionic or amphoteric surface-active agent or a mixture thereof; a thickening agent; a perfume; a sequestering agent; a film-forming agent; a treatment agent; a dispersing agent; a conditioning agent; a preservative; an opacifying agent; and an agent for swelling keratinous fibers.

29. A composition for dyeing keratinous fibers comprising in a medium suitable for dyeing keratinous fibers (a) at least one indole derivative having the formula

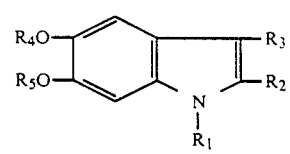

(I)

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or —COOSi$R_6R_7R_8$, $R_4$ and $R_5$, each independently, represent hydrogen, linear or branched $C_1$-$C_{20}$ alkyl, formyl, linear or branched $C_2$-$C_{20}$ acyl, linear or branched $C_3$-$C_{20}$ alkenoyl, —Si$R_6R_7R_8$, —P(O)(O$R_9$)$_2$ or $R_9$OSO$_2$, or $R_4$ and $R_5$ together with the oxygen atoms to which they are attached form a ring optionally containing a carbonyl group, a methylene group, a thiocarbonyl group, a

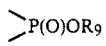

group or a

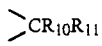

group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole derivative being present in an amount ranging from 0.01 to 5 percent by weight based on the total weight of said composition, (b) at least one quinone dye selected from the group consisting of (i) 1,4-hydroxynaphthoquinone having the formula

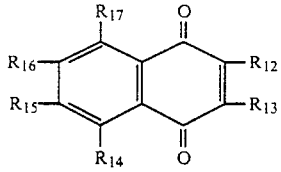

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

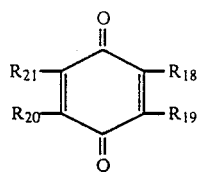

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ represent methyl, hydroxy or methoxy, at least one of the other substituents is other than hydrogen, and that when two of $R_{18}$, $R_{19}$, and $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4-trihydroxyanthraquinone, 1,2,7-trihydroxyanthraquinone, 1,2,5,8-tetrahydroxyanthraquinone, 3-carboxy-1,2,4-trihydroxyanthraquinone, 2-carboxy-1-methyl-3,5,6,8-tetrahydroxyanthraquinone, 3-sulpho-1,2,4-trihydroxyanthraquinone, 3-sulpho-1,2,-dihydroxyanthraquinone, 5,8-dichloro-1,4-dihydroxyanthraquinone and 3-hydroxymethylanthraquinone, said quinone dye being present in an amount ranging from 0.01 to 5 percent by weight based on the total weight of said composition, and (c) a source of iodide ions or a nitrite source.

30. The composition of claim 29 wherein said quinone dye is selected from the group consisting of 2-hydroxy-1,4-napthoquinone, 2,5-dihydroxy-1,4-naphthoquinone, 2-hyroxy-3-methyl-1,4-naphthoquinone, 2-hydroxy-3-methoxy-1,4-naphthoquinone, 2,3-dihydroxy-1,4,-naphthoquinone, 2,5,7-trihydroxy-1,4-naphthoquinone, 5-hydroxy-1,4-naphthoquinone, 2,5,8-trihydroxy-1,4,-naphthoquinone, 2,5-dihydroxy-3-methyl-1,4,-naphthoquinone, 2,5-dihydroxy-3-methyl-1,4.-benzoquinone, 2,5-dihydroxy-3-methoxy-6-methyl-1,4-benzoquinone, 2-carboxyl-1-methyl-3,5,6,8-tetrahydroxyanthraquinone, 1,2-dihydroxyanthraquinone, 1,2,4-trihydroxyanthraquinone and 3-carboxyl-1,2,4-trihydroxyanthraquinone.

31. A multicompartment kit for use in dyeing keratinous fibers comprising a first compartment housing composition (A) containing components (a) and (b) as defined in claim 34 and and in said first compartment or in a second compartment, part or all of the oxidizing system defined in claim 1.

32. The multicompartment kit of claim 31 wherein said composition (A) housed in said first compartment contains a source of iodide ions and said second compartment houses an aqueous hydrogen peroxide composition having a pH ranging from 2 to 12.

33. The multicompartment kit of claim 31 which also contains a third compartment housing an aqueous medium for admixture at the time of use with the contents of said first compartment housing composition (A) in an anhydrous solvent medium.

34. The multicompartment kit of claim 31 wherein said first compartment houses said composition (A) containing components (a) and (b) and said second compartment houses, in an aqueous medium suitable for dyeing keratinous fibers, a permanganate, a dichromate or a periodate.

35. The multicompartment kit of claim 31 wherein said first compartment houses said composition (A) containing components (a) and (b) and said second compartment houses, in an aqueous medium suitable for dyeing keratinous fibers and having an acidic pH, a nitrite source.

36. The multicompartment kit of clai 31 wherein said first compartment houses said composition (A) containing components (a) and (b) and a nitrite source and said second compartment houses an acidic aqueous composition.

37. A process for dyeing keratinous fibers comprising applying to said fibers at least one composition (A) containing in a medium suitable for dyeing said fibers, (a) at least one indole derivative having the formula

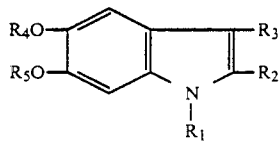

(I)

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or $-COOSiR_6R_7R_8$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $R_9OSO_2$, or $R_4$ and $R_5$ together with the oxygen atoms to which they are attached form a ring optionally containing a carbonyl group, a methylene group, a thiocarbonyl group, a

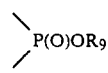

group or a

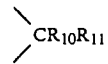

group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole derivative being present in said composition (A) in an amount ranging from 0.01 to 5 percent by weight based on the total weight of said composition (A), (b) at least one quinone dye selected from the group consisting of (i) 1,4-hydroxynaphthoquinone having the formula

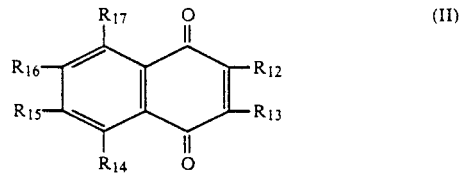

(II)

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

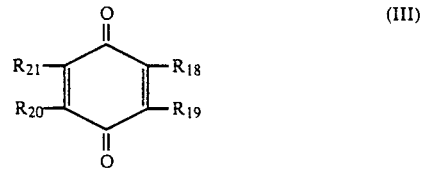

(III)

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4-trihydroxyanthraquinone, 1,2,7-trihydroxyanthraquinone, 1,2,5,8-tetrahydroxyanthraquinone, 3-carboxy-1,2,4-trihydroxyanthraquinone, 2-carboxyl-1-methyl-3,5,6,8-tetrahydroxyanthraquinone, 3-sulpho-1,2,4-trihydroxyanthraquinone, 3-sulpho-1,2-dihydroxyanthraquinone, 5,8-dichloro-1,4-dihydroxyanthraquinone and 3-hydroxymethylanthraquinone, said quinone dye being present in said composition (A) in an amount ranging from 0.01 to 5 percent by weight based on the total weight of said composition (A), developing a color on said fibers using as an oxidizing system, a source of iodide ions and hydrogen peroxide, in which case said composition (A) contains either (a) a source of iodide ions or (b) hydrogen peroxide and the application of said composition (A) is preceded or followed by the application of composition (B) comprising in a medium suitable for dyeing said fibers (a') hydrogen peroxide at a pH ranging from 2 to 12 when said composition (A) contains a source of iodide ions, or (b') a source of iodide ions at a pH ranging from 3 to 11 when said composition (A) contains hydrogen peroxide, said source of iodide ions being potassium iodide.

38. A process for dyeing keratinous fibers comprising applying to said fibers at least one composition (A) containing in a medium suitable for dyeing said fibers, (a) at least one indole derivative having the formula

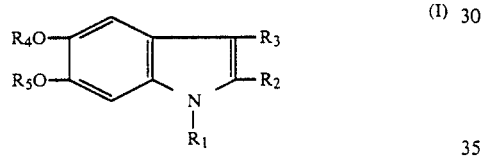
(I)

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or $-COOSiR_6R_7R_8$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $R_9OSO_2$, or $R_4$ and $R_5$ together with the oxygen atoms to which they are attached form a ring optionally containing a carbonyl group, a methylene group, a thiocarbonyl group, a

group or a

group, $R_9$ and $R_{10}$ represent hydrogen or lower alkyl,
$R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole derivative being present in said composition (A) in an amount ranging from 0.01 to 5 percent by weight based on the total weight of said composition (A), (b) at least one quinone dye selected from the group consisting of (i) 1,4-hydroxynaphthoquinone having the formula

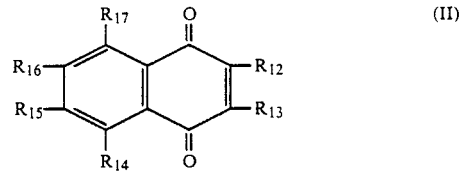
(II)

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

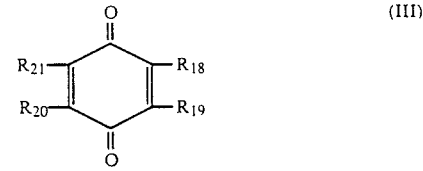
(III)

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4-trihydroxyanthraquinone, 1,2,7-trihydroxyanthraquinone, 1,2,5,8-tetrahydroxyanthraquinone, 3-carboxyl-1,2,4-trihydroxyanthraquinone, 2-carboxy-1-methyl-3,5,6,8-tetrahydroxyanthraquinone, 3-sulpho-1,2,4-trihydroxyanthraquinone, 3-sulpho-1,2-dihydroxyanthraquinone, 5,8-dichloro-1,4-dihydroxyanthraquinone and 3-hydroxymethylanthraquinone, said quinone dye being present in said composition (A) in an amount ranging from 0.01 to 5 percent by weight based on the total weight of said composition (A), developing a color on said fibers using as an oxidizing system, a nitrite source, in which case the application of said composition (A) is followed by the application of composition (B') comprising an aqueous composition having an acidic pH, said composition (A) or said composition (B') containing at least one said nitrite source, said nitrite source being selected from the group consisting of an alkali metal nitrite, an alkaline earth metal nitrite, an ammonium nitrite, or an organic nitrite.

39. A process for dyeing keratinous fibers comprising applying to said fibers at least one composition (A) containing in a medium suitable for dyeing said fibers, (a) at least one indole derivative having the formula

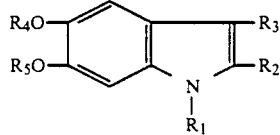

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or $-COOSiR_6R_7R_8$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $R_9OSO_2$, or $R_4$ and $R_5$ together with the oxygen atoms to which they are attached form a ring optionally containing a carbonyl group, a methylene group, a thiocarbonyl group, a

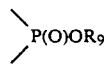

group or a

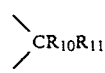

group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole derivative being present in said composition (A) in an amount ranging from 0.01 to 5 percent by weight based on the total weight of said composition (A), (b) at least one quinone dye selected from the group consisting of (i) 1,4-hydroxynaphthoquinone having the formula

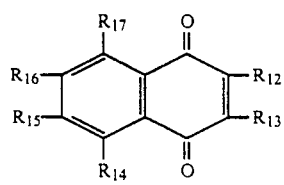

wherein when $R_{12}$ represents OH, $R_{13}$ represents hydrogen, halogen, hydroxyl, alkoxy, nitro, alkyl or acyl, and $R_{14}$, $R_{15}$, $R_{16}$ and $R_{17}$, each independently, represent hydrogen, hydroxyl, alkoxy, alkyl or acyl; or when $R_{14}$ represents OH, $R_{12}$ and $R_{13}$, each independently, represent hydrogen, methyl, methoxy, nitro or halogen; $R_{15}$ and $R_{16}$, each independently, represent hydrogen, hydroxyl, methyl or methoxy; and $R_{17}$ represents hydrogen, methyl or methoxy;

(ii) a benzoquinone derivative having the formula

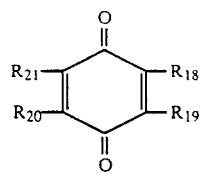

wherein $R_{18}$, $R_{19}$, $R_{20}$ and $R_{21}$, each independently, represent hydrogen, hydroxyl, alkoxy, alkyl, hydroxylated alkyl, phenyl, or OH-substituted phenyl, with the provisos that at least one of $R_{18}$, $R_{19}$, $R_{20}$ and $R_{21}$ is other than hydrogen and that $R_{18}$ and $R_{21}$, or $R_{19}$ and $R_{20}$ are not alkyl simultaneously, and that when one of $R_{18}$, $R_{19}$, $R_{20}$ and $R_{21}$ represents methyl, hydroxy or methoxy, at least one of the other substituents is other than hydrogen, and that when two of $R_{18}$, $R_{19}$, $R_{20}$ and $R_{21}$ are identical and are situated para relative to each other and represent hydroxyl or methoxy, at least one of the other two substituents is other than hydrogen; and (iii) a hydroxyanthraquinone selected from the group consisting of 1,2-dihydroxyanthraquinone, 1,4-dihydroxyanthraquinone, 1,2,4- trihydroxyanthraquinone, 1,2,7-trihydroxyanthraquinone, 1,2,5,8-tetrahydroxyanthraquinone, 3-carboxyl-1,2,4-trihydroxyanthraquinone, 2-carboxy-1-methyl-3,5,6,8-tetrahydroxyanthraquinone, 3-sulpho-1,2,4-trihydroxyanthraquinone, 3-sulpho-1,2,-dihydroxyanthraquinone, 5,8-dichloro-1,4,-dihydroxyanthraquinone and 3-hydroxymethylanthraquinone,
said quinone dye being present in said composition (A) in an amount ranging from 0.01 to 5 percent by weight based on the total weight of said composition (A), applied to said fibers simultaneously or sequentially, separately in a composition (B'') comprising a medium suitable for dyeing said fibers and said sodium periodate.

* * * * *